United States Patent
Natsume et al.

(10) Patent No.: US 9,239,228 B2
(45) Date of Patent: Jan. 19, 2016

(54) WAFER MAPPING APPARATUS AND LOAD PORT INCLUDING SAME

(71) Applicant: SINFONIA TECHNOLOGY CO., LTD., Minato-ku (JP)

(72) Inventors: Mitsuo Natsume, Minato-ku (JP); Masahiro Osawa, Minato-ku (JP); Toshimitsu Morihana, Minato-ku (JP); Mitsutoshi Ochiai, Minato-ku (JP)

(73) Assignee: SINFONIA TECHNOLOGY CO., LTD., Minato-ku (JP)

( * ) Notice: Subject to any disclaimer, the term of this patent is extended or adjusted under 35 U.S.C. 154(b) by 0 days.

(21) Appl. No.: 14/689,551

(22) Filed: Apr. 17, 2015

(65) Prior Publication Data

US 2015/0308812 A1    Oct. 29, 2015

(30) Foreign Application Priority Data

Apr. 28, 2014    (JP) .................. 2014-092924

(51) Int. Cl.
| | | |
|---|---|---|
| *G01N 21/64* | (2006.01) | |
| *G01B 11/14* | (2006.01) | |
| *G01B 11/24* | (2006.01) | |
| *G01B 11/00* | (2006.01) | |
| *G01N 35/10* | (2006.01) | |
| *G01B 11/22* | (2006.01) | |

(52) U.S. Cl.
CPC .............. *G01B 11/002* (2013.01); *G01N 21/64* (2013.01); *G01B 11/14* (2013.01); *G01B 11/22* (2013.01); *G01B 11/24* (2013.01); *G01N 35/1016* (2013.01); *G01N 2035/1025* (2013.01)

(58) Field of Classification Search
USPC ............. 356/237.1–241.6, 242.1–243.8, 356/426–431, 600–640
See application file for complete search history.

(56) References Cited

U.S. PATENT DOCUMENTS

| | | | | | |
|---|---|---|---|---|---|
| 5,308,993 | A | * | 5/1994 | Holman | .................. G01V 8/24 250/223 R |
| 6,147,356 | A | * | 11/2000 | Hahn | .................... H01L 21/681 250/559.29 |
| 6,188,323 | B1 | * | 2/2001 | Rosenquist | ....... H01L 21/67265 340/686.5 |
| 6,303,939 | B1 | * | 10/2001 | Chung | ............. H01L 21/67265 250/559.29 |
| 6,542,839 | B1 | * | 4/2003 | Lu | ..................... H01L 21/67259 250/559.33 |
| 7,105,847 | B2 | * | 9/2006 | Oka | .................. H01L 21/67265 250/559.29 |

(Continued)

FOREIGN PATENT DOCUMENTS

| | | |
|---|---|---|
| JP | 4096213 | 6/2008 |
| JP | 4246420 | 4/2009 |
| JP | 4501755 | 7/2010 |

(Continued)

*Primary Examiner* — Kara E Geisel
*Assistant Examiner* — Jarreas C Underwood
(74) *Attorney, Agent, or Firm* — Oblon, McClelland, Maier & Neustadt, L.L.P.

(57) ABSTRACT

The left-right span between a light projection section 5a and a light receiving section 5b of a mapping sensor 5 having an optical axis L1 extending in a left-right horizontal direction is arranged to be narrower than the span of a front opening of a open cassette 12 which is a smaller one of differently-sized containers conveyed to a load port, and the mapping sensor is attached to a mapping device 4. A first protrusion sensor 6 having an optical axis L2 extending in the left-right horizontal direction is attached to the mapping device 4 to be separated from the mapping sensor 5 in a moving direction of the mapping sensor 5. Furthermore, a second protrusion sensor 7 having an optical axis extending in the up-down moving direction of the mapping sensor 5 is provided.

5 Claims, 5 Drawing Sheets

(56) References Cited

U.S. PATENT DOCUMENTS

2003/0119214 A1\* 6/2003 Kitazawa .......... H01L 21/67265
　　　　　　　　　　　　　　　　　　　438/5
2012/0067770 A1　3/2012 Hatano et al.

FOREIGN PATENT DOCUMENTS

| JP | 4866315 | 2/2012 |
| JP | 2012-064827 | 3/2012 |
| JP | 2015-050410 | 3/2015 |

\* cited by examiner

WAFER MAPPING APPARATUS AND LOAD PORT INCLUDING SAME

CROSS REFERENCE TO RELATED APPLICATION

The present application claims priority from Japanese Patent Application No. 2014-092924, which was filed on Apr. 28, 2014, the disclosure of which is herein incorporated by reference in its entirety.

BACKGROUND OF THE INVENTION

The present invention relates to a wafer mapping apparatus which is configured to recognize semiconductor wafers (hereinafter simply referred to as wafers) stored in a container which is to be conveyed to a load port, and relates also to a load port including the wafer mapping apparatus.

In a semiconductor manufacturing process, a container storing wafers from which semiconductor devices are manufactured is conveyed to a load port which is provided at an entrance of a processing room which is a clean environment therein, and after a door of the load port is opened, the wafers stored in the container are taken into the processing room by a robot or the like. In the container, the wafers are placed on vertically-aligned shelves in the container.

Wafer size has recently increased in accordance with the increased production of semiconductors, and wafers which are 450 mm in diameter will be in use. Currently-popular large wafers which are 300 mm in diameter are stored in a sealed container termed a FOUP (Front Open Unified Pod) and conveyed to a load port. A front opening of the sealed container is connected with an entrance of a processing room in a sealed condition. A lid of the container is opened together with a door of the load port, and the wafers are taken into the processing room (see e.g., Patent Literatures 1 to 3 (Patent Literature 1: Japanese Patent No. 4246420, Patent Literature 2: Japanese Patent No. 4501755, and Patent Literature 3: Japanese Patent No. 4866315)). Previously-popular small wafers which are, for example, 200 mm in diameter are typically stored in an open container termed an open cassette and conveyed, and are taken into a processing room through a load port, in a clean room (see e.g., Patent Literature 4 (Patent Literature 4: Japanese Patent No. 4096213)).

When wafers are taken from a container such as the FOUP and the open cassette described above into a processing room, a wafer mapping apparatus which maps and recognizes the state of the wafers in the container is used, in order to allow a robot or the like to automatically take the wafers. The wafer mapping apparatus is arranged in such a way that, a transmission optical sensor having a horizontally-extending optical axis is, as a mapping sensor, attached to a leading end portion of a mapping device such as a mapping arm and a mapping frame, which device is movable forward, backward, upward, and downward. After the mapping device is moved forward to insert the mapping sensor into the front opening of the container, the mapping sensor is moved in an up-down direction in the container. In this way, the wafer mapping apparatus detects the wafers stored in vertically-aligned shelves. The mapping device is attached to a moving mechanism which is able to linearly move in an up-down direction. As this linear moving mechanism, an elevatable door of a load port may be used.

Such a wafer mapping apparatus is provided with a protrusion sensor which detects a wafer which protrudes forward from the back side of a shelf, in order to prevent in advance of the collision of the wafer with the mapping sensor which moves in the up-down direction in the container (see e.g., Patent Literatures 1 to 4). As the protrusion sensor, Patent Literature 1 recites a transmission optical sensor which is attached to the fixed frame of the door of the load port so that the optical axis of the sensor extends in the up-down direction. As the protrusion sensor, furthermore, Patent Literature 2 recites two transmission optical sensors which are attached to a mapping frame which is movable in the up-down direction so that the optical axis of each sensor extends in the up-down direction, whereas Patent Literature 4 recites a transmission optical sensor which is attached to a mapping arm so that the optical axis of the sensor horizontally extends. Furthermore, Patent Literature 3 recites that, as a first protrusion sensor, a transmission optical sensor is attached to the fixed frame of the door of the load port so that the optical axis of the sensor extends in the up-down direction, and as a second protrusion sensor, a transmission optical sensor is attached to a mapping arm to have a horizontally-extending optical axis. This second protrusion sensor is provided not for preventing the collision of the wafer with the mapping sensor. This sensor is an intermediate sensor for detecting misregistration of wafers which are taken by a robot or the like.

In the meanwhile, it has been demanded to modify a load port which deals with currently-popular wafers stored in a FOUP and 300 mm in diameter to be able to deal with wafers stored in an open cassette and 200 mm in diameter. In response to such demand, there is a proposal that a closed cassette adopter is provided to cover the outside of an open cassette for wafers with 200 mm diameter, the cassette adopter is attached to a load port for wafers with 300 mm diameter, and the wafers with 200 mm diameter stored in the open cassette are taken into a processing room in a sealed condition. To put it differently, the cassette adopter and the FOUP for 300-mm wafers are positioned at the same position and connected with the entrance of the processing room in a sealed condition, and the 200-mm wafers stored in the open cassette and the 300-mm wafers stored in the FOUP are taken into the processing room by a shared robot or the like (see e.g., Patent Literature 5 (Japanese Unexamined Patent Publication No. 2012-64827)).

SUMMARY OF THE INVENTION

As described in Patent Literature 5, when differently-sized wafers stored in differently-sized containers are dealt with by a common load port, common use of a single wafer mapping apparatus recited in Patent Literatures 1 to 4 involves the following problem.

FIG. 5 is a schematic view showing, on a single plane, differently-sized wafers W1 and W2 which are stored in differently-sized containers C1 and C2, respectively, the containers C1 and C2 being positioned with respect to a common load port. The central leading ends of the wafers W1 and W2 are adjusted to be at the same position to allow a common robot or the like to take these wafers. The left-right span S1 of a mapping sensor of the common wafer mapping apparatus is required to be shorter than the opening span S2 of the container C2 to allow the mapping sensor to be inserted into the smaller container C2. On this account, as shown in the figure, while the periphery of the smaller wafer W2 is sufficiently far from the mapping sensor, the periphery of the larger wafer W1 is very close to the mapping sensor. The larger wafer W1 may therefore collide with the mapping sensor S which is movable in the up-down direction, even with slight protrusion of the wafer.

The collision of the larger wafer W1 with the mapping sensor may occur, when the wafer W1 protrudes only slightly in the container but the position of the central leading end of the wafer is still inside the container C1. On this account, as described in Patent Literatures 1 and 3, the transmission optical sensor which is attached to the fixed frame of the door of the load port so that the optical axis of the sensor extends in the up-down direction cannot be employed as the protrusion sensor, because this sensor is not able to detect a wafer W1 which slightly protrudes in the container.

In the meanwhile, a transmission optical sensor attached to a mapping arm or a mapping frame which is inserted into a container, e.g., the protrusion sensor recited in the Patent Literatures 2 and 4, is able to detect a wafer protruding in a container. However, this protrusion sensor, which moves in the up-down direction in the container, may itself collide with a slightly-protruding wafer.

For the reasons above, the known wafer mapping apparatus recited in Patent Literatures 1 to 4 cannot be commonly used for the load port recited in Patent Literature 5, which deals with differently-sized wafers. To deal with differently-sized wafers, plural wafer mapping apparatuses which are suitable for respective containers may be used. However, when plural wafer mapping apparatuses are used, the structure of the load port is complicated. Furthermore, because the number of actuators in the mapping device is increased, the clean processing room tends to be contaminated by foreign matters such as abrasion powder generated from the actuators.

An object of the present invention is therefore to arrange a load port dealing with differently-sized wafers to be able to employ a common wafer mapping apparatus.

To achieve the object above, the present invention employs a wafer mapping apparatus for commonly mapping differently-sized wafers which are conveyed to a load port and stored in differently-sized containers, which includes: a mapping sensor which emits a detection wave having a radiation axis extending in a left-right horizontal direction, a left-right span of the mapping sensor being narrower than a span of a front opening of a minimum-sized container among the differently-sized containers, and the mapping sensor being inserted into a front opening of each of the containers and moving in an up-down direction in each of the containers to detect the wafers stored in each of the containers; a mapping device which is movable in the up-down direction, the mapping sensor being attached to the mapping device; a first protrusion sensor which emits a detection wave having a radiation axis extending in the left-right horizontal direction, and is attached to the mapping device to be separated frontward from the mapping sensor in a moving direction of the mapping sensor so as to detect a protrusion of a wafer stored in each of the containers; and a second protrusion sensor which emits a detection wave having a radiation axis extending in an up-down moving direction of the mapping sensor, and detects a protrusion of a wafer stored in each of the containers.

To put it differently, a protruding wafer which may collide with the mapping sensor is detected by the first protrusion sensor, whereas a protruding wafer which may collide with the first protrusion sensor which moves in front of the mapping sensor is detected by the second protrusion sensor. This allows a load port dealing with differently-sized wafers to be able to employ a common wafer mapping apparatus, while preventing the collision of a wafer with the mapping sensor and/or the protrusion sensor. In addition to the above, because in this wafer mapping apparatus the number of a actuators in one mapping device is small, the generation of abrasion powder which contaminates a processing room is restrained.

Examples of the detection waves emitted from the mapping sensor and the first and second protrusion sensors include light waves, electromagnetic waves, and supersonic waves.

Because the distance between the first protrusion sensor and the mapping sensor is arranged to be equal to or longer than the braking distance in the up-down moving direction of the mapping device, collision of the mapping sensor with a wafer is certainly prevented.

Because the irradiation axis of the second protrusion sensor is, at a central portion in a left-right direction of the front opening span of each of the containers, arranged to be farther from the containers than the radiation axis of the first protrusion sensor, collision of the second protrusion sensor with a wafer is prevented.

In addition to the above, the present invention employs a load port including one of the above-described wafer mapping apparatuses.

In the wafer mapping apparatus of the present invention, a protruding wafer which may collide with the mapping sensor is detected by the first protrusion sensor, whereas a protruding wafer which may collide with the first protrusion sensor which moves in front of the mapping sensor is detected by the second protrusion sensor. This allows a load port dealing with differently-sized wafers to be able to employ a common wafer mapping apparatus, while preventing the collision of a wafer with the mapping sensor and/or the protrusion sensor. In addition to the above, because in this wafer mapping apparatus the number of a actuators in one mapping device is small, the generation of abrasion powder which contaminates a processing room is restrained.

DESCRIPTION OF THE PREFERRED EMBODIMENTS

Figure 1:
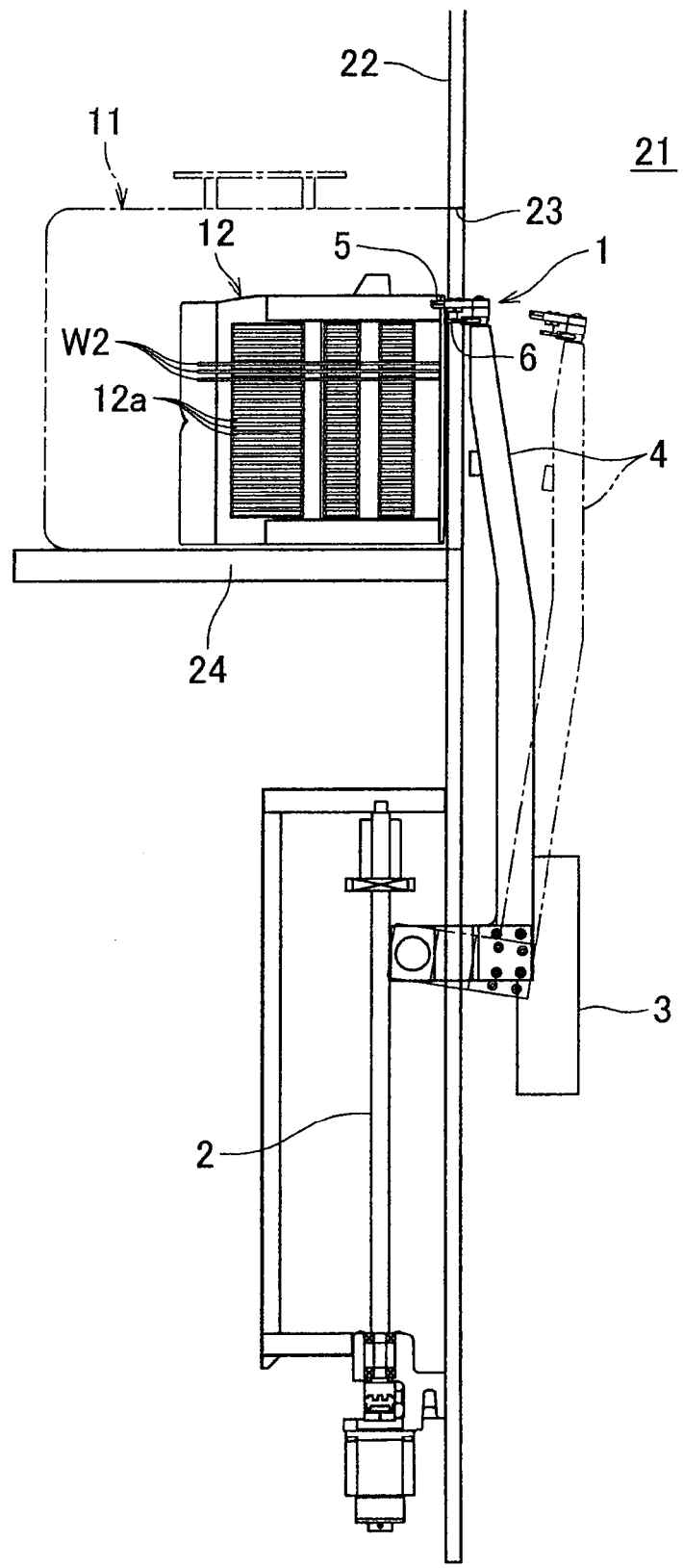
FIG. 1 is a longitudinal cross sectional side view of a load port including a wafer mapping apparatus of the present invention.
Figure 2:
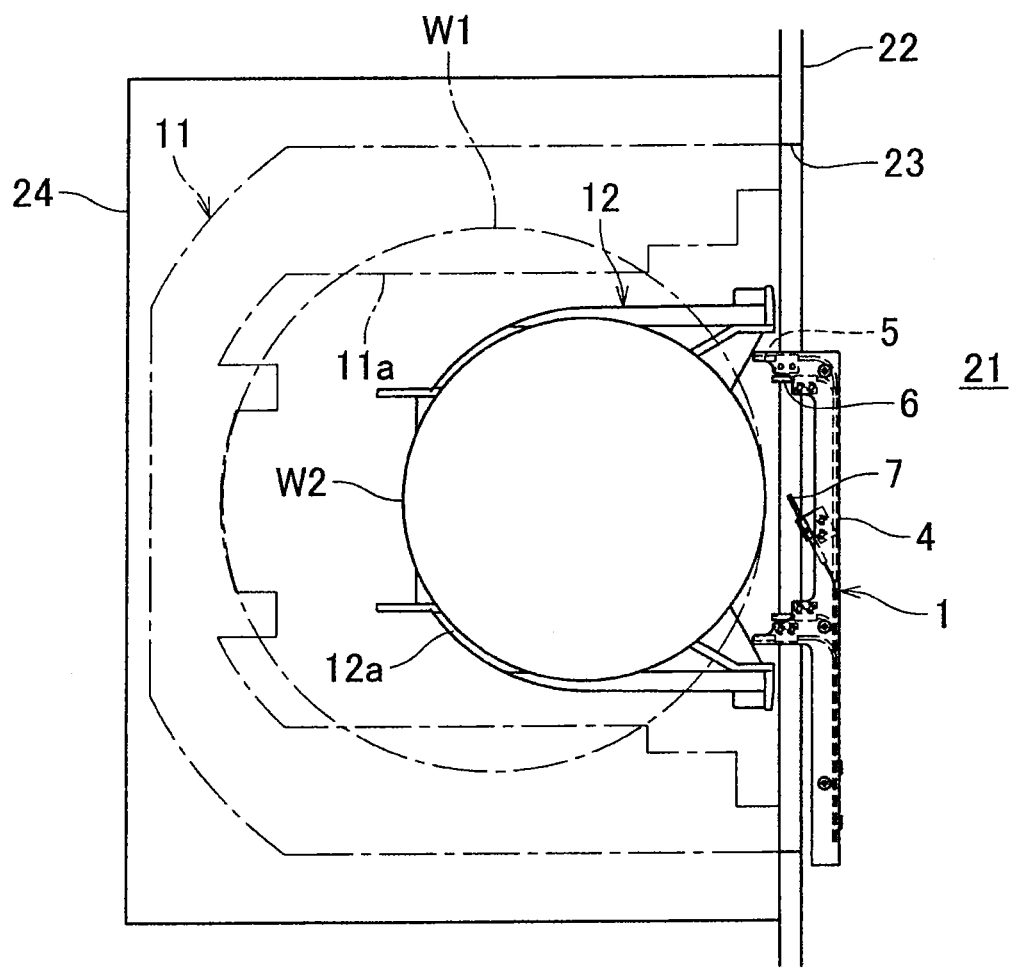
FIG. 2 is a cross sectional plan view of FIG. 1.

The following will describe an embodiment of the present invention with reference to figures. FIG. 1 and FIG. 2 show a load port of the present invention, which includes a wafer mapping apparatus 1. This load port deals with both wafers W1 which are stored in a FOUP 11 and 300 mm in diameter and wafers W2 which are stored in an open cassette 12 and 200 mm in diameter. In this load port, a table 24 on which the conveyed FOUP 11 and/or open cassette 12 is placed is provided in front of an entrance 23 formed through a shielding wall 22 of a processing room 21 which is arranged to be a clean environment.

In FIG. 1 and FIG. 2, a case where the wafers W2 which are stored in the open cassette 12 and 200 mm in diameter are dealt with is indicated by full lines, whereas a case where the wafers W1 which are stored in the FOUP 11 and 300 mm in diameter are dealt with is indicated by dashed lines. The wafers W1 and W2 are stored in vertically-aligned shelves 11a and 12a of the FOUP 11 and the open cassette 12. The open cassette 12 is housed in a sealed cassette adopter (not illustrated) having a front opening which is identical in size with the FOUP 11, and is positioned on the table 24. A front opening of the cassette adopter from which a lid has been removed together with a door of the entrance 23 of the processing room 21 is connected with the entrance 23 of the processing room 21 in a sealed condition, and the stored wafers W2 are taken into the processing room 21 by a robot (not illustrated). When the wafers W1 which are stored in the FOUP 11 and 300 mm in diameter are dealt with, a front opening of the FOUP 11 is connected with the entrance 23 of the processing room 21 in a similar manner, and the stored wafers W1 are taken into the processing room 21 by the common robot.

At the entrance 23 of the processing room 21, the wafer mapping apparatus 1 is provided to map and recognize the wafers W1 and W2 stored in the FOUP 11 and the open cassette 12 before the wafers W1 and W2 are taken out by the robot. This wafer mapping apparatus 1 is arranged in such a manner that, a mapping sensor 5, a first protrusion sensor 6, and a second protrusion sensor 7 are attached to a leading end portion of a mapping device 4 which is linearly moved in the up-down direction by a ball screw 2 and inclined forward by an air cylinder 3 to be inserted into the front opening of the FOUP 11 or the open cassette 12.

Figure 3:
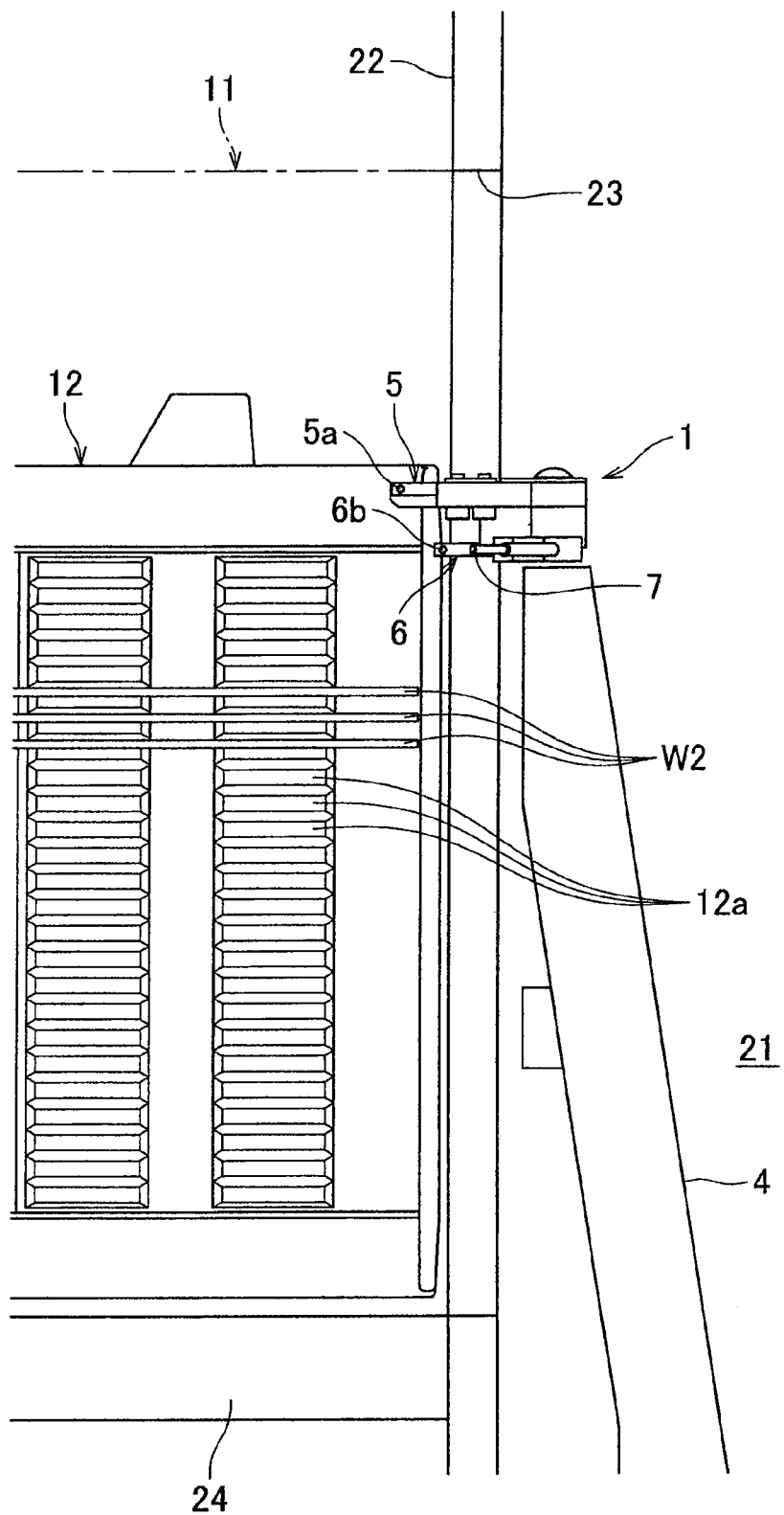
FIG. 3 is an enlarged side view of an important part of FIG. 1.
Figure 4:
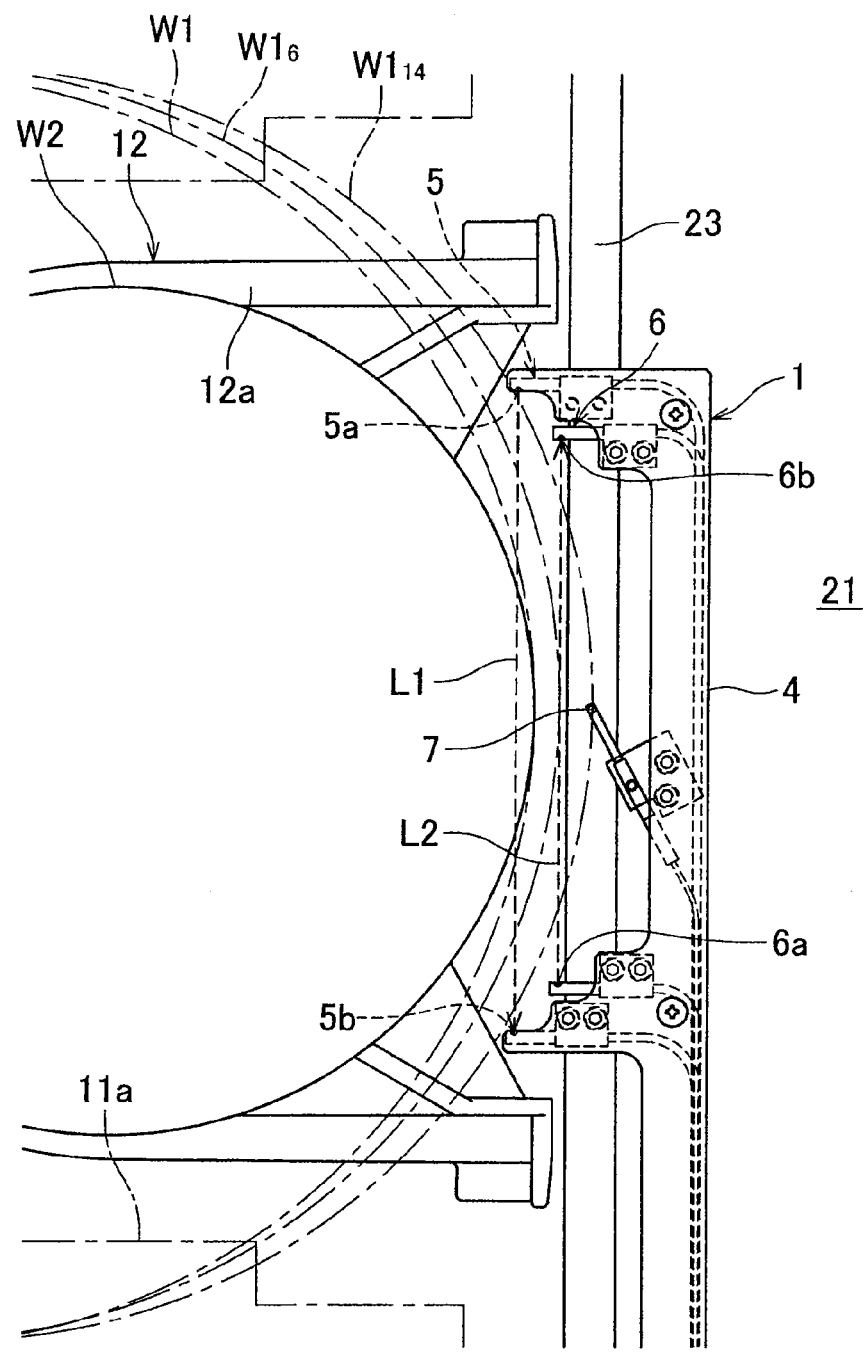
FIG. 4 is an enlarged plan view of an important part of FIG. 2.
Figure 5:
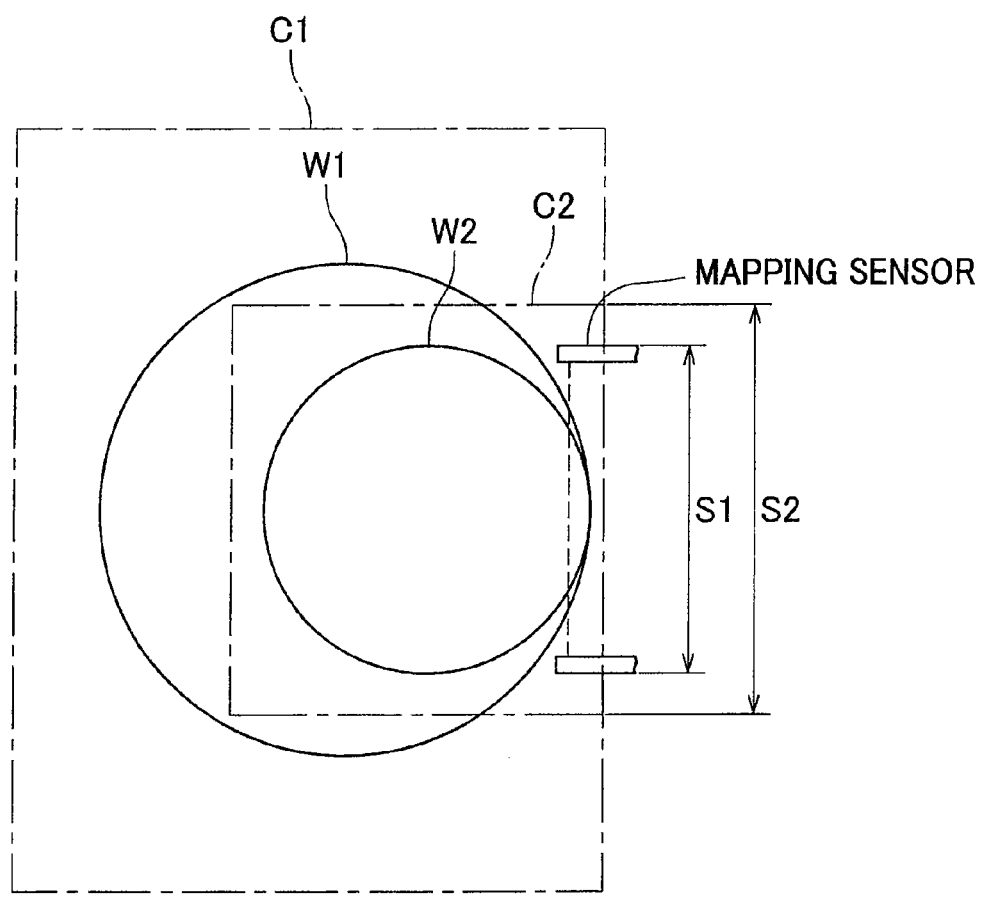
FIG. 5 is a schematic view showing, on a single plane, differently-sized wafers which are stored in containers with a common load port.

FIG. 3 and FIG. 4 are enlarged views of important parts of FIG. 1 and FIG. 2, i.e., around the front opening of the open cassette 12 and around the leading end portion of the mapping device 4. The central leading end of the 300-mm wafer W1 and the central leading end of the 200-mm wafer W2 are arranged to be at the same position to allow the common robot to take the both types of wafers.

The mapping sensor 5 is a transmission optical sensor which is provided with a light projection section 5a and a light receiving section 5b on the left and right sides and has an optical axis L1 which is the irradiation axis of a detection wave and extends in the left-right horizontal direction. To allow the mapping sensor 5 to be inserted into the open cassette 12 which is the smaller container, the span between the light projection section 5a and the light receiving section 5b is arranged to be narrower than the left-right span (210 mm) of the front opening of the open cassette 12. It is noted that the left-right span (365 mm) of the front opening of the FOUP is very long and is not depicted in FIG. 4. In the present embodiment, the span between the light projection section 5a and the light receiving section 5b of the mapping sensor 5 is arranged to be 154 mm. The left-right span of this mapping sensor 5 is arranged to be between 105 mm which is the span of a wafer mapping apparatus for a known open cassette and 200 mm which is slightly shorter by a margin than 210 mm which is the span of the front opening of the open cassette 12.

The mapping sensor 5 moves downward to detect the wafers W1 and W2 stored in the shelves 11a and 12a of the FOUP 11 and the open cassette 12.

The first protrusion sensor 6 is also a transmission optical sensor which is provided with a light projection section 6a and a light receiving section 6b and has an optical axis L2 extending in the left-right horizontal direction. This first protrusion sensor 6 is provided below the mapping sensor 5 to be separated from the mapping sensor 5 by at least the braking distance of the ball screw 2 which moves the mapping device 4. The first protrusion sensor 6 is slightly closer to the entrance 23 than the mapping sensor 5, and the light projection section 6a, and the light receiving section 6b of the first protrusion sensor 6 are reversed left and right as compared to the light projection section 5a and the light receiving section 5b of the mapping sensor 5. The direction of the optical axis L2 is opposite to the direction of the optical axis L1 of the mapping sensor 5. Because the optical axis L1 of the mapping sensor 5 and the optical axis L2 of the first protrusion sensor 6 are arranged to be opposite to each other as above, interference between sets of light entering the respective light receiving sections 5b and 6b is prevented.

The first protrusion sensor 6 moves in front of the mapping sensor 5 in the moving direction of the mapping sensor 5, so as to detect a protruding wafer W1 or W2 which may collide with the mapping sensor 5. When the first protrusion sensor 6 detects a protruding wafer W1 or W2, the ball screw 2 by which the mapping device 4 is moved is stopped.

The second protrusion sensor 7 is a reflection optical sensor in which an optical axis which is the irradiation axis of a detection wave extends downward in which direction the mapping sensor 5 moves. This second protrusion sensor 7 is provided at a central part in the left-right direction of the front opening of the open cassette 12 and is closer to the entrance 23 than the optical axis L2 of the first protrusion sensor 6. The second protrusion sensor 7 is attached to be substantially flush with the first protrusion sensor 6, and the detection range of this sensor 7 is arranged to be equal to or longer than the braking distance of the ball screw 2. The second protrusion sensor 7 detects a protruding wafer W1 or W2 which may collide with the first protrusion sensor 6 which moves in front of the sensor 5 in the moving direction of the sensor 5. The ball screw 2 is stopped also when the second protrusion sensor 7 detects a protruding wafer W1 or W2.

As shown in FIG. 4, while the periphery of the 200-mm wafer W2 is sufficiently far from the mapping sensor 5, the periphery of the 300-mm wafer W1 is very close to the mapping sensor 5. On this account, when the 300-mm wafers W1 are mapped, the mapping sensor 4 collides with a protruding wafer W1 even if the degree of protrusion of the wafer W1 is slight. FIG. 4 additionally shows a wafer $W1_6$ which protrudes by 6 mm and may collide with the mapping sensor 5 and a wafer $W1_{14}$ which protrudes by 14 mm and may collide with the first protrusion sensor 6.

In the present embodiment, the first protrusion sensor 6 is positioned in the front-back direction to be able to detect a wafer W1 which protrudes equally with or more than the wafer $W1_6$ which protrudes by 6 mm. In the meanwhile, the second protrusion sensor 7 is positioned in the front-back direction to be able to detect a wafer W1 which protrudes equally with or more than the wafer $W1_{14}$ which protrudes by 14 mm. As such, the first protrusion sensor 6 detects a wafer W1 which may collide with the mapping sensor 5, whereas the second protrusion sensor 7 detects a wafer W1 which may collide with the first protrusion sensor 6. Although not illustrated, the length with which collision with the mapping sensor 5 or the first protrusion sensor 6 may occur is much longer in the case of the 200-mm wafer W2. However, in a manner similar to the above, the first protrusion sensor 6 detects a wafer W2 which may collide with the mapping sensor 5, and the second protrusion sensor 7 detects a wafer W2 which may collide with the first protrusion sensor 6.

While in the embodiment above the wafers with two sizes, i.e., 300 mm and 200 mm in diameter, are commonly dealt with, the sizes of wafers which are dealt with by the load port of the present invention are not limited to those described in the embodiment above. For example, when wafers which are 450 mm and 300 mm in diameter are dealt with, the left-right span of the mapping sensor is arranged to be between 200 mm which is the span of a wafer mapping apparatus for a 300-mm FOUP and 350 mm which is slightly shorter by a margin than 365 mm which is the span of a front opening for a 450-mm FOUP. Furthermore, wafers with three or more sizes may be commonly dealt with. In this case, the left-right span of the mapping sensor is arranged to be narrower than the span of the front opening of the container which stores smallest wafers.

While in the embodiment above the mapping sensor is moved downward, the mapping sensor may be moved upward. In this case, the first protrusion sensor is provided above the mapping sensor to be separated from the mapping sensor, and the optical axis of the second protrusion sensor is arranged to extend upward.

While in the embodiment above the second protrusion sensor is attached to the mapping device in such a way that the second protrusion sensor is at a central portion in the left-right direction of the front opening of the container and is substantially flush with the first protrusion sensor, the position in the height direction of the second protrusion sensor is not limited to the embodiment above. The position in the height direction may be changed on condition that the detection range of the second protrusion sensor reaches a position in front of the first protrusion sensor in the moving direction of the first protrusion sensor. Furthermore, the position in the left-right direction is not limited to the central portion. Furthermore, the second protrusion sensor may be fixed to, for example, the frame of the door of the load port. Alternatively, the second protrusion sensor may be attached to the mapping device, and a third protrusion sensor may be attached to, for example, the frame of the door of the load port.

While in the embodiment above the mapping sensor and the first protrusion sensor are transmission optical sensors whereas the second protrusion sensor is a reflection optical sensor, each of the mapping sensor and the first protrusion sensor may be a reflection optical sensor in which a light projection section and a light receiving section are provided on one side whereas a reflection mirror is provided on the other side. Furthermore, the second protrusion sensor may be a transmission optical sensor in which a light projection section is provided on one side whereas a light receiving section is provided on the other side. These transmission and reflection optical sensors may employ, as the detection waves, electromagnetic waves, supersonic waves, or the like.

While in the embodiment above the dedicated mapping device which is movable in the up-down direction is provided, the mapping device may be moved in the up-down direction by a conveyance robot which takes wafers. Furthermore, the mapping device may be embedded in an EFEM (Equipment Front End Module) which is a wafer conveyance system including a load port and a conveyance robot.

What is claimed is:

1. A wafer mapping apparatus for commonly mapping differently-sized wafers which are conveyed to a load port and stored in differently-sized containers, the wafer mapping apparatus comprising:

a mapping sensor which emits a detection wave having a radiation axis extending in a left-right horizontal direction, a left-right span of the mapping sensor being narrower than a span of a front opening of a minimum-sized container among the differently-sized containers, and the mapping sensor being inserted into a front opening of each of the containers and moving in an up-down direction in each of the containers to detect the wafers stored in each of the containers;

a mapping device which is movable in the up-down direction, the mapping sensor being attached to the mapping device;

a first protrusion sensor which emits a detection wave having a radiation axis extending in the left-right horizontal direction, and is attached to the mapping device to be separated frontward from the mapping sensor in a moving direction of the mapping sensor so as to detect a protrusion of a wafer stored in each of the containers; and a second protrusion sensor which emits a detection wave having a radiation axis extending in an up-down moving direction of the mapping sensor, and detects a protrusion of a wafer stored in each of the containers.

2. The wafer mapping apparatus according to claim 1, wherein, the distance between the first protrusion sensor and the mapping sensor is equal to or longer than a braking distance in the up-down moving direction of the mapping device.

3. The wafer mapping apparatus according to claim 1, wherein, at a central portion of the left-right span of the front opening of each of the containers, the radiation axis of the second protrusion sensor is farther from the containers than the radiation axis of the first protrusion sensor.

4. The wafer mapping apparatus according to claim 1, wherein, the distance between the first protrusion sensor and the mapping sensor is equal to or longer than a braking distance in the up-down moving direction of the mapping device, and at a central portion of the left-right span of the front opening of each of the containers, the radiation axis of the second protrusion sensor is farther from the containers than the radiation axis of the first protrusion sensor.

5. A load port comprising the wafer mapping apparatus of claim 1.

* * * * *